United States Patent
Kim et al.

(10) Patent No.: US 10,870,619 B2
(45) Date of Patent: Dec. 22, 2020

(54) METHOD FOR PREPARING L-METHIONINE CRYSTALS USING CRYSTALLIZATION TECHNIQUE

(71) Applicant: CJ CHEILJEDANG CORPORATION, Seoul (KR)

(72) Inventors: Jun-Woo Kim, Gyeonggi-do (KR); In Sung Lee, Seoul (KR); Kee Kahb Koo, Seoul (KR); Wang Soo Kim, Seoul (KR); Allan S. Myerson, Cambridge, MA (US)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/469,852

(22) PCT Filed: Dec. 29, 2017

(86) PCT No.: PCT/KR2017/015709
§ 371 (c)(1),
(2) Date: Jun. 14, 2019

(87) PCT Pub. No.: WO2018/124803
PCT Pub. Date: Jul. 5, 2018

(65) Prior Publication Data
US 2019/0315682 A1    Oct. 17, 2019

(30) Foreign Application Priority Data
Dec. 30, 2016 (KR) ........................ 10-2016-0183571

(51) Int. Cl.
*C07C 319/28* (2006.01)
*B01D 9/00* (2006.01)
*C07C 323/58* (2006.01)

(52) U.S. Cl.
CPC .......... *C07C 319/28* (2013.01); *B01D 9/0063* (2013.01); *C07C 323/58* (2013.01); *B01D 2009/0086* (2013.01); *C07B 2200/13* (2013.01)

(58) Field of Classification Search
CPC ................ C07C 323/58; C07C 319/28; B01D 2009/0086; B01D 9/00; B01D 9/0063; B01D 2009/009; B01D 9/005; C07B 2200/13
See application file for complete search history.

(56) References Cited

U.S. PATENT DOCUMENTS

| 5,463,120 A | 10/1995 | Giraud et al. |
| 2005/0089975 A1* | 4/2005 | Lorbert ............... C12P 13/12 435/113 |

FOREIGN PATENT DOCUMENTS

| CN | 104152524 A | 11/2014 |
| JP | 2000-143617 A | 5/2000 |
| JP | 2004-175715 A | 6/2004 |
| JP | 2004-292324 A | 10/2004 |
| KR | 10-2000-0076040 A | 12/2000 |
| KR | 10-2006-0103337 A | 3/2009 |
| KR | 10-2003-7001521 A | 6/2009 |
| KR | 10-2012-0129994 A | 11/2012 |
| KR | 10-2014-0138946 A | 12/2014 |

OTHER PUBLICATIONS

International Search Report dated Apr. 16, 2018 from International Application No. PCT/KR2017/015709, 5 pages with English translation.
Matsuoka, M. et al, "Polymorphis, morphologies and bulk densities of DL-methionine agglomerate crystals", Journal of Crystal Growth, 1999, vol. 198, No. 199, pp. 1299-1309.

* cited by examiner

*Primary Examiner* — Jafar F Parsa
*Assistant Examiner* — Blaine G Doletski
(74) *Attorney, Agent, or Firm* — MH2 Technology Law Group, LLP

(57) ABSTRACT

The present application relates to a method for preparing L-methionine crystals with an improved bulk density. As the L-methionine crystals prepared according to the method for preparing L-methionine crystals of the present application may have a bulk density of up to 800 g/L, the L-methionine crystals are expected to reduce storage and transport costs of L-methionine powder and improve working conditions due to improved fluidity of the powder.

11 Claims, 6 Drawing Sheets

[FIG. 1]
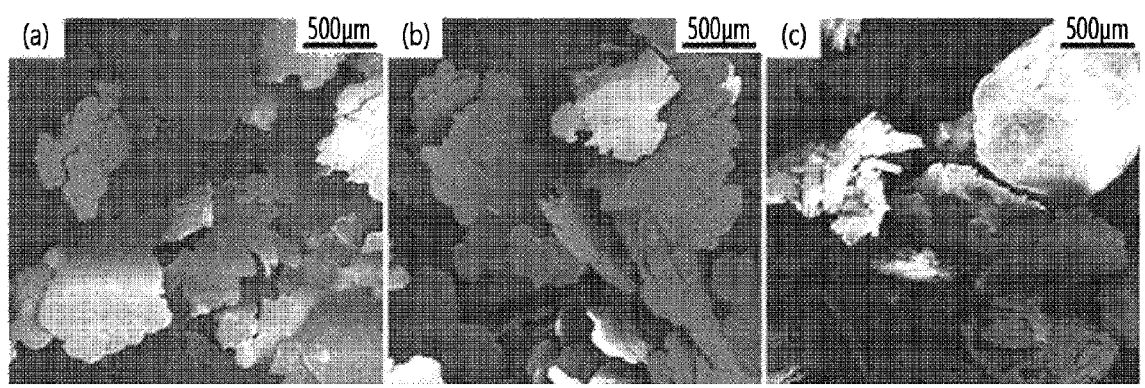

[FIG. 2]
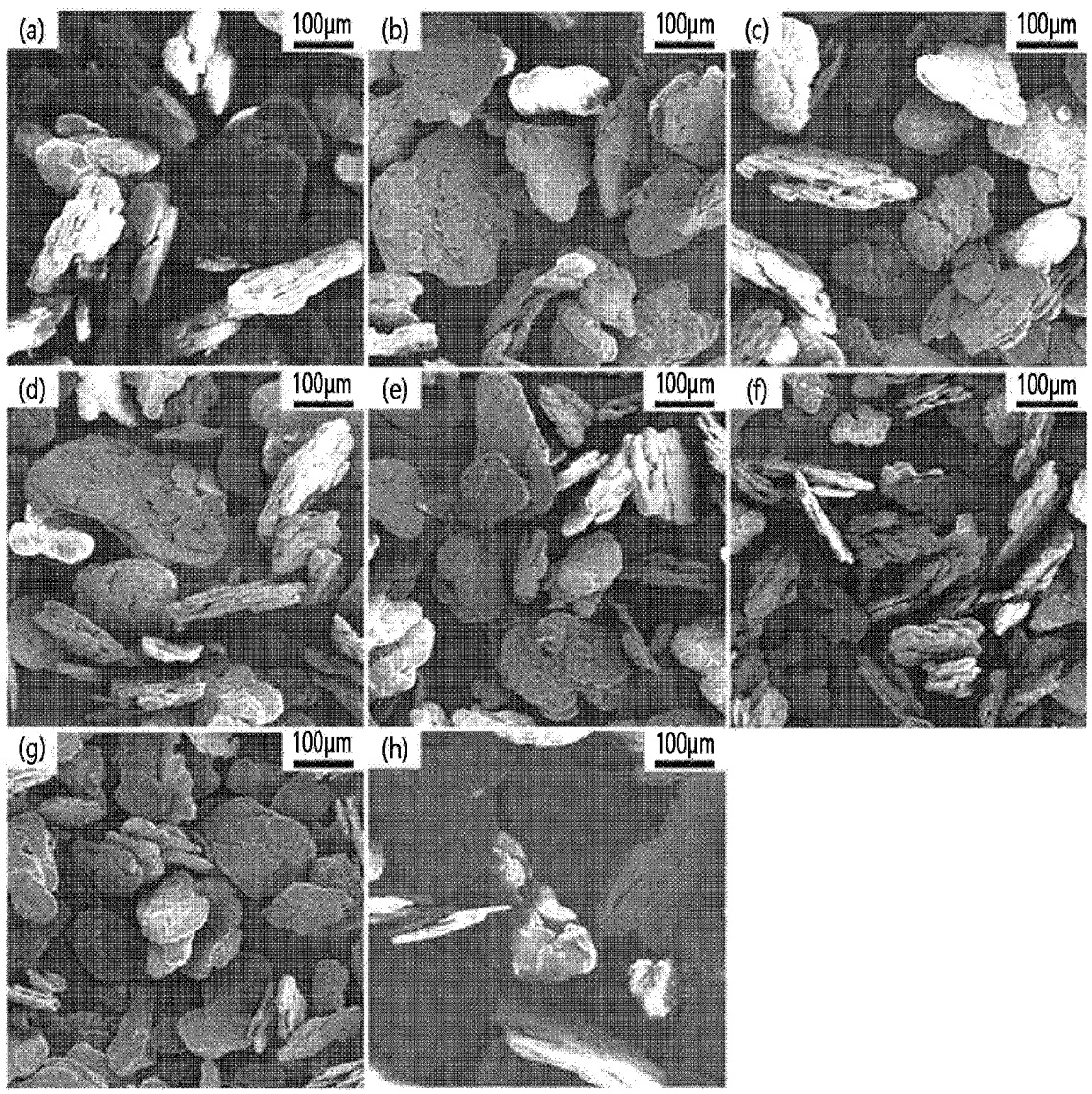

[FIG. 3]
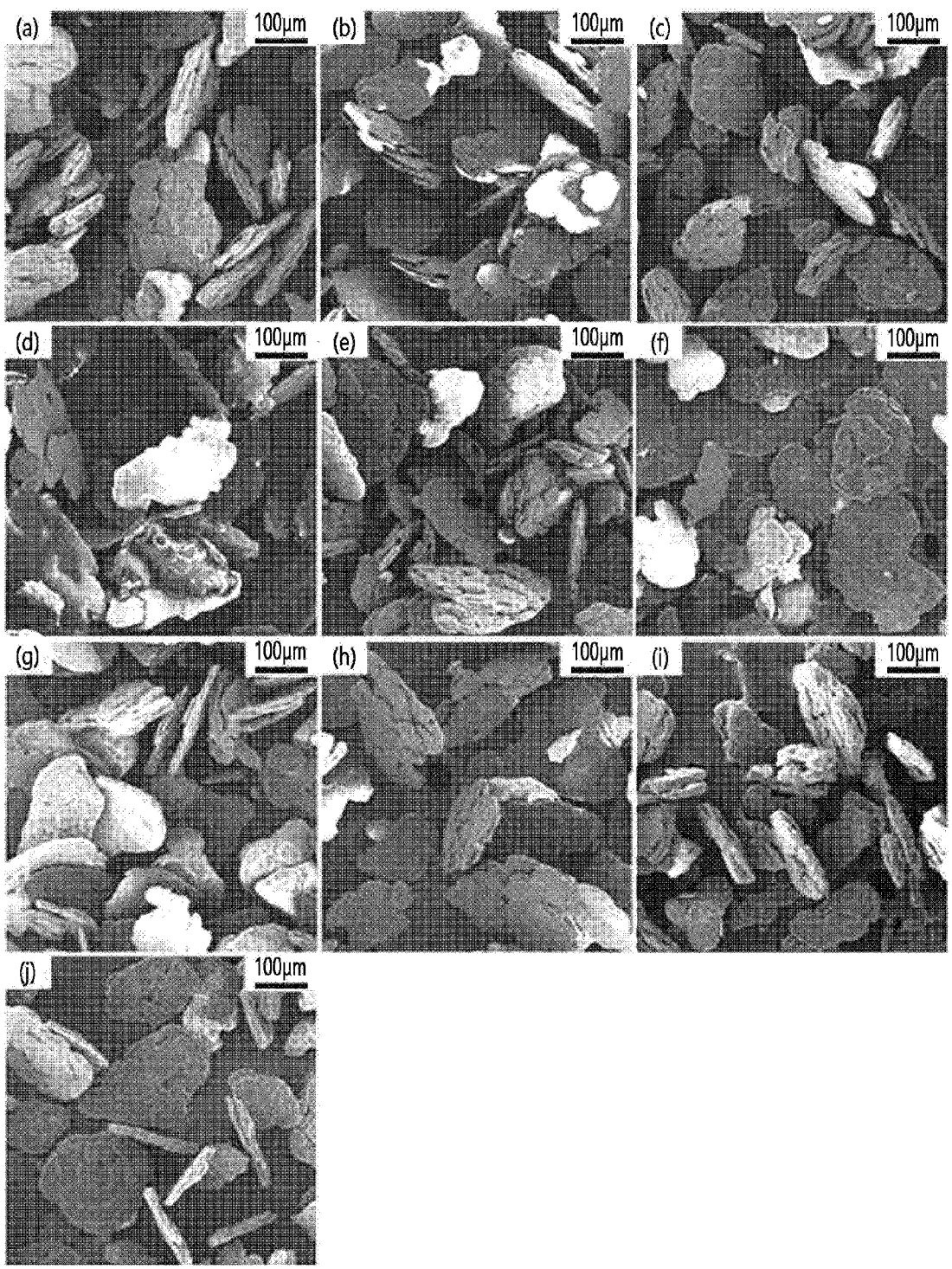

[FIG. 4]
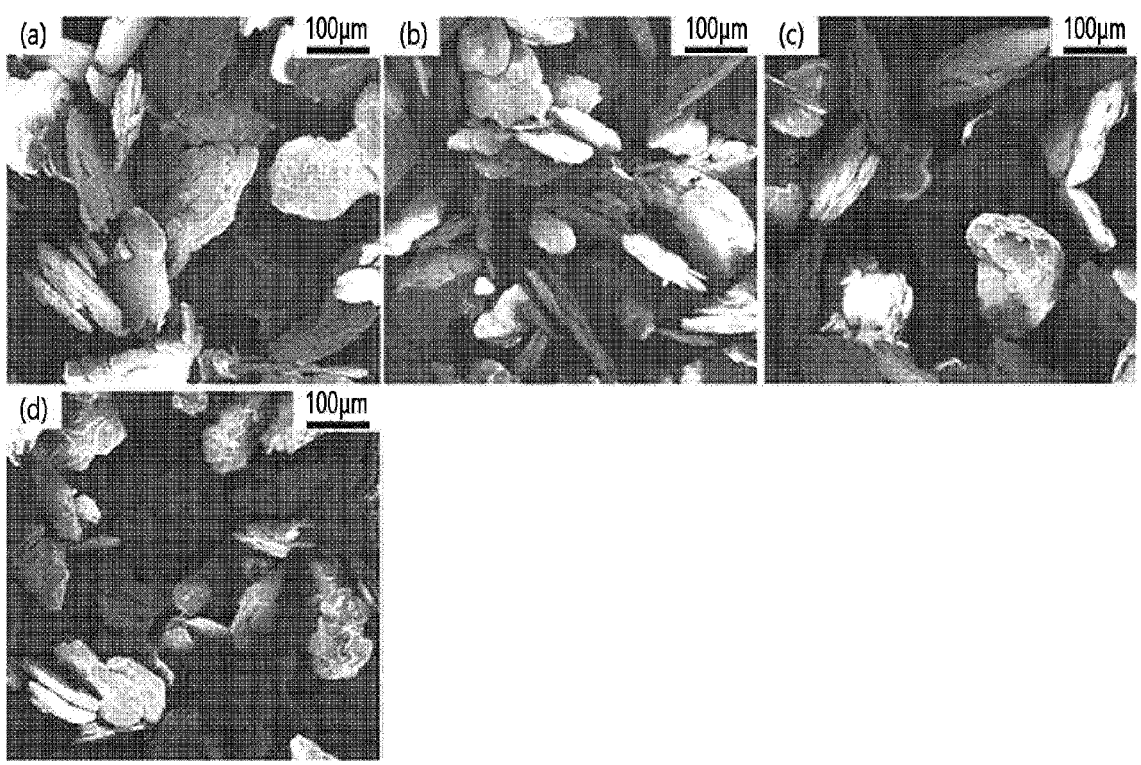

[FIG. 5]
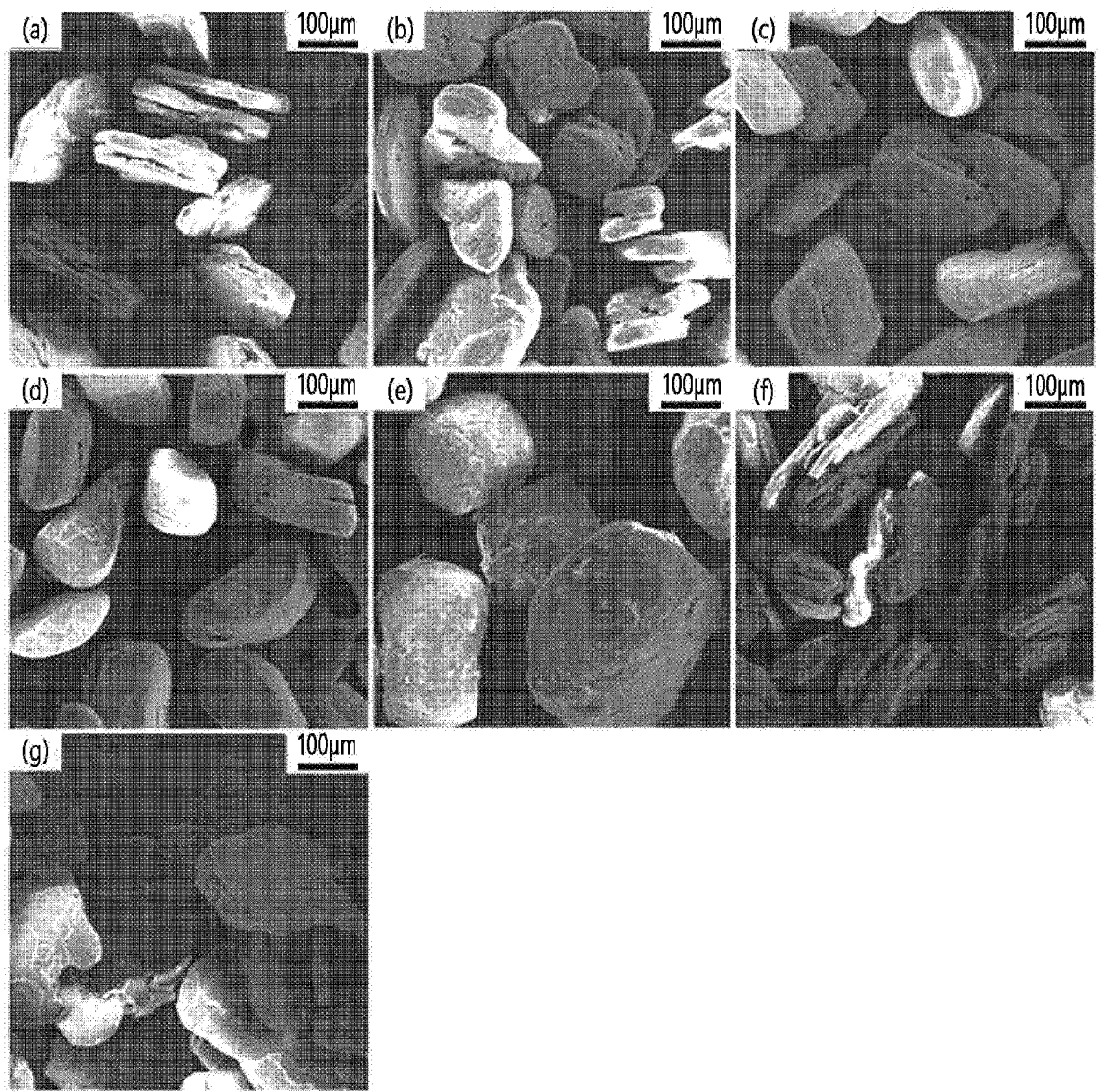

[FIG. 6]
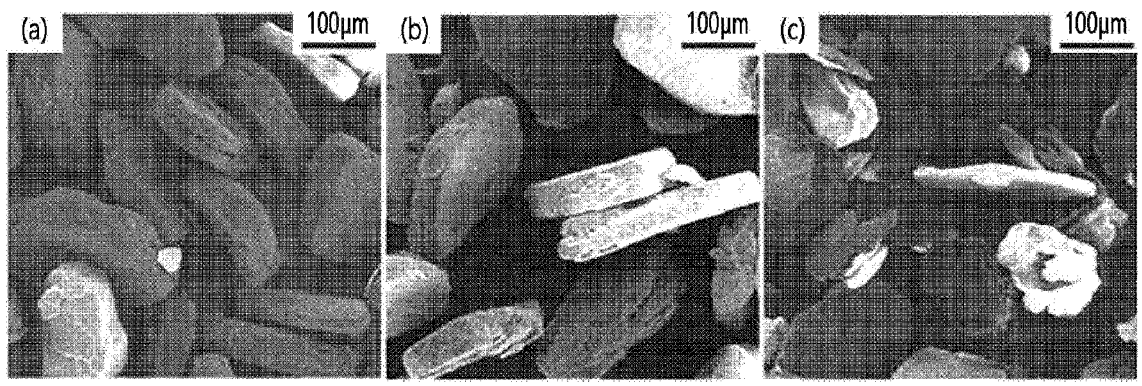
[FIG. 7]
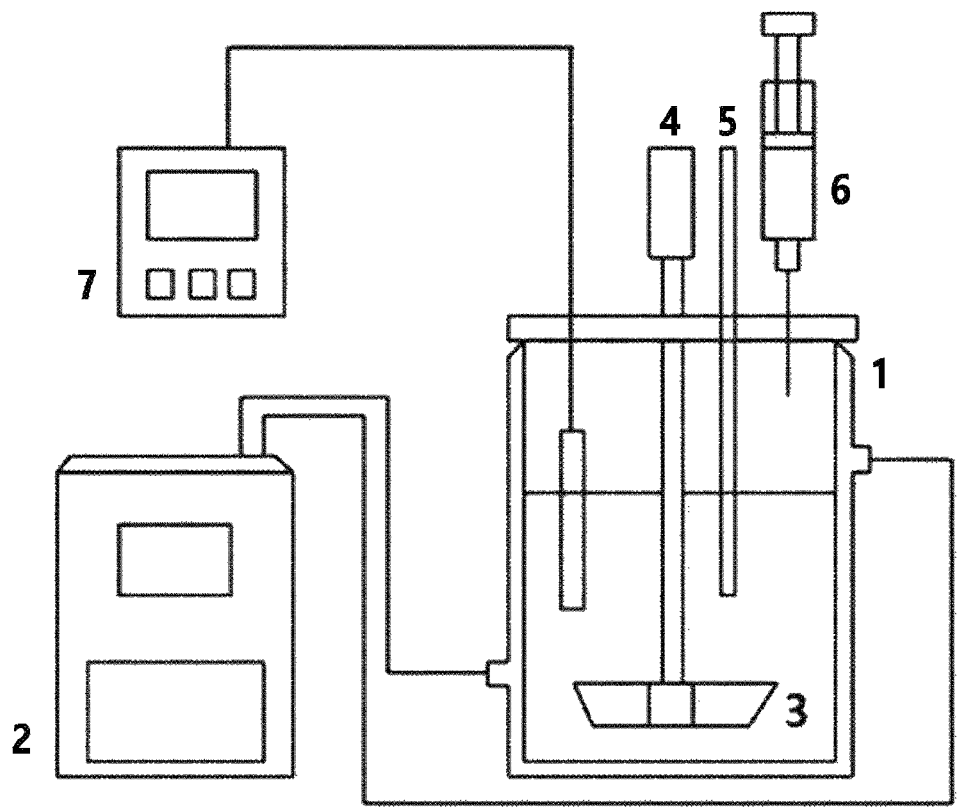

METHOD FOR PREPARING L-METHIONINE CRYSTALS USING CRYSTALLIZATION TECHNIQUE

CROSS-REFERENCE TO RELATED APPLICATIONS

This application is a U.S. National Stage application of PCT/KR2017/015709 filed 29 Dec. 2017, which claims priority to Korean Patent Application No. 10-2016-0183571 filed 30 Dec. 2016, the entire disclosures of which are herein incorporated by reference.

TECHNICAL FIELD

The present disclosure relates to a method for preparing L-methionine crystals with an increased bulk density, and more specifically, a method for preparing L-methionine crystals, in which the bulk density of the L-methionine crystals is increased using crystallization techniques, such as pH adjustment, heating, and cooling of an aqueous solution of L-methionine.

BACKGROUND ART

Crystallization is a separation technique used to obtain from a solution a desired solute in a solid state, and this process has been widely applied to obtain amino acid crystals with high purity. If it is possible to prepare powder with a large bulk density using the crystallization technique, enhancement of operational conditions can also be expected due to cost reduction in the storage and transportation of the powder and improvement of the powder's rheological characteristics.

Meanwhile, it is generally known that methionine crystals are difficult to stabilize because they are flaky, and coagulants are required for crystallization. However, even when these coagulants are used, there is still a limitation with regard to the increase of the bulk density of methionine crystals, and studies to increase the bulk density of methionine crystals are underway.

Attempts to increase the bulk density continue to be made. Examples of these attempts include: a method for preparing methionine granules, in which methionine powder, water, a binding agent, and a surfactant are mixed and a high shear rate is applied to the mixture (Korean Patent Application Publication No. 2003-7001521); a method for improving a bulk density by a recrystallization method in which a high-temperature methionine solution is injected into a low-temperature methionine suspension (Japanese Patent Application Publication No. 2004-292324); a method for preparing methionine by performing the method disclosed in Japanese Patent Application Publication No. 2004-292324 in a continuous manner (Korean Patent Application Publication No. 2014-0138946), etc. However, the method for preparing methionine crystals with a satisfactory bulk density has not yet been developed.

DISCLOSURE

Technical Problem

The present inventors have made efforts to develop a method for preparing L-methionine crystals with an increased bulk density, and as a result, they have confirmed that the bulk density of L-methionine crystals can be significantly increased when L-methionine crystals are prepared using a crystallization process, in which the pH of an aqueous solution of L-methionine is adjusted, the aqueous solution is heated, a coagulant is added, the pH of the aqueous solution is readjusted and/or the solution is cooled, etc., thereby completing the present disclosure.

Technical Solution

An object of the present disclosure is to provide a method for preparing L-methionine crystals with an improved bulk density.

Another object of the present disclosure is to provide L-methionine crystals prepared according to the above method of preparing L-methionine crystals.

Advantageous Effects

The method for preparing L-methionine crystals of the present disclosure can significantly improve the bulk density of L-methionine compared to other existing methods for preparing L-methionine crystals known in the art.

BRIEF DESCRIPTION OF DRAWINGS

FIG. 1 shows SEM images of L-methionine crystals, in which panels 1(a) and 1(b) show the SEM images of L-methionine crystals obtained according to Examples 1 and 2 of the present disclosure, and panel 1(c) shows the SEM image of L-methionine crystals obtained according to Comparative Example 1 of the present disclosure.

FIG. 2 shows SEM images of L-methionine crystals, in which panels 2(a) to 2(g) show the SEM images of L-methionine crystals obtained according to Examples 3 to 9 of the present disclosure, respectively, and panel 2(h) shows the SEM image of L-methionine crystals obtained according to Comparative Example 2 of the present disclosure.

FIG. 3 shows SEM images of L-methionine crystals, in which all of the images on the left of FIG. 3 are the SEM images of L-methionine crystals obtained according to Examples, whereas all of the images on the right of FIG. 3 are the SEM images of L-methionine crystals obtained according to Comparative Examples. Specifically, panels 3(a), 3(c), 3(e), 3(g), and 3(i) show the SEM images of L-methionine crystals obtained according to Examples 10 to 14 of the present disclosure, respectively, and panels 3(b), 3(d), 3(f), 3(h), and 3(j) show the SEM images of L-methionine crystals obtained according to Comparative Examples 3 to 7 of the present disclosure.

FIG. 4 shows SEM images of L-methionine crystals, in which panels 4(a) and 4(c) show the SEM images of L-methionine crystals obtained according to Examples 15 and 16 of the present disclosure, and panels 4(b) and 4(d) show the SEM images of L-methionine crystals obtained according to Comparative Examples 8 and 9 of the present disclosure.

FIG. 5 shows SEM images of L-methionine crystals, in which panels 5(a) to 5(e) show the SEM images of L-methionine crystals obtained according to Examples 17 to 21 of the present disclosure, respectively, and panels 5(f) and 5(g) show the SEM images of L-methionine crystals obtained according to Comparative Examples 10 and 11 of the present disclosure.

FIG. 6 shows SEM images of L-methionine crystals, in which panel 6(a) shows the SEM image of L-methionine crystals obtained according to Example 22 of the present disclosure, and panels 6(b) and 6(c) show the SEM images of L-methionine crystals obtained according to Comparative Examples 12 and 13 of the present disclosure.

FIG. 7 shows a schematic diagram illustrating the constitution of an apparatus capable of performing the method for preparing L-methionine crystals of the present disclosure. As illustrated, the apparatus includes a jacket crystallizer 1, a thermostat 2, an impeller 3, a stirrer 4, a thermometer 5, a pH adjuster injector 6, and a pH meter 7.

BEST MODE FOR CARRYING OUT THE INVENTION

To develop a method for preparing L-methionine crystals with an improved bulk density, the present inventors have developed a method using a pH control agent in the process of crystallizing L-methionine. The method for preparing L-methionine crystals of the present disclosure can significantly improve the bulk density of L-methionine compared to other existing methods for preparing L-methionine crystals known in the art.

The present disclosure is described in detail as follows. Meanwhile, respective descriptions and embodiments disclosed in the present disclosure may also be applied to other descriptions and embodiments. That is, all combinations of various elements disclosed in the present disclosure fall within the scope of the present invention. Further, the scope of the present invention is not limited by the specific description below.

To achieve the above objects, an aspect of the present disclosure provides a method for preparing L-methionine crystals, which includes: (a) adding a pH control agent to an aqueous solution containing L-methionine to lower or increase the pH (a step of pH adjustment); (b) heating the aqueous solution containing L-methionine (a step of heat treatment); and (c) extracting L-methionine crystals from the aqueous solution containing L-methionine, which underwent pH adjustment and heat treatment (a step of extraction of crystals).

As used herein, "L-methionine" may be obtained by chemical synthesis or biological synthesis via microbial fermentation, but the method of L-methionine synthesis is not limited thereto. The method for preparing L-methionine crystals of the present disclosure may include (a) a step of pH adjustment; (b) a step of heat treatment; and (c) a step of extraction of crystals, and through these steps, L-methionine crystals which are uniform in size and have a high bulk density can be prepared in high yield.

As used herein, the term "bulk density" refers to the density measured based on the volume including voids generated between particles when powder is filled into a container. In particular, the density of powder which is measured after treating the powder by tapping a cylinder filled with the powder with a constant force so as to make the powder within the cylinder dense is called tapped bulk density (hereinafter, "BD"). Although the bulk density confirmed in Examples of the present disclosure was "BD", it is apparent to those skilled in the art that the bulk density, tapped bulk density, and "BD" are proportional to one another, and thus, these terms are used interchangeably in the present disclosure. Hereinafter, the method for preparing L-methionine crystals will be described in detail.

Step (a) is a step of adding a pH control agent to an aqueous solution containing L-methionine to lower or increase the pH, and in the present disclosure, Step (a) is named "a step of pH adjustment".

In Step (a), the aqueous solution containing L-methionine may be an aqueous solution in which L-methionine is dissolved in water; or a fermentation liquid of a microorganism containing L-methionine, an enzyme reaction solution, or a chemical reaction solution, but the aqueous solution is not limited thereto.

Additionally, the aqueous solution containing L-methionine may contain a material other than L-methionine, but the material to be contained is not limited thereto.

Additionally, the aqueous solution containing L-methionine may specifically contain L-methionine in an amount of 20 to 60 parts by weight, more specifically 35 to 50 parts by weight, relative to 300 parts by weight of water, but the amount of L-methionine is not limited thereto and L-methionine may be contained in an appropriate amount by those skilled in the art according to the pH control agent to be added and subsequent processes.

Additionally, the L-methionine in the aqueous solution containing L-methionine may be in a state where L-methionine is dissolved completely or part of the L-methionine is not dissolved.

As used herein, the term "pH control agent" refers to a material which is added to a solution to adjust the pH, and it may contain both a pH decreasing agent for decreasing the pH and a pH increasing agent for increasing the pH. In the present disclosure, it was confirmed that only the inclusion of a step of adding a pH control agent to an aqueous solution containing L-methionine during the process of preparing L-methionine crystals significantly increases the bulk density of the prepared L-methionine crystals. That is, the technical feature of the method for preparing the L-methionine crystals of the present disclosure lies in that the method includes a pH adjustment step. The technical feature is not limited to any one of decreasing pH or increasing pH, but it should be understood that the addition of a pH control agent to an aqueous solution containing L-methionine causes a change in pH (i.e., a decrease or increase of pH) of the solution, and as a result, according to the increase of solubility of L-methionine, those effects appear in which the bulk density of L-methionine crystals (i.e., final product) increase and the recovery rate due to the increase of the amount of initial input of methionine increases.

In the present disclosure, the pH-lowering agent is not limited as long as it can lower the pH of the aqueous solution into which the pH-lowering agent is added, and specifically, the pH-lowering agent may be a $H^+$ donor or $OH^-$ acceptor. The $H^+$ donor includes all of the materials capable of donating hydrogen ions to other materials, and may be a strong acid material (e.g., sulfuric acid, hydrochloric acid, etc.), but the $H^+$ donor is not limited thereto. Additionally, the $OH^-$ acceptor includes all of the materials capable of accepting hydroxide ions of other materials, and specifically an aqueous solution of an ammonium salt, but the $OH^-$ acceptor is not limited thereto.

In the present disclosure, the pH-increasing agent may not be limited as long as it can increase the pH of the aqueous solution into which the pH-lowering agent is added, and specifically, the pH-increasing agent may be a H+ acceptor or $OH^-$ donor. The $H^+$ acceptor includes all of the materials capable of accepting hydrogen ions of other materials, and specifically, the H+ acceptor may be an aqueous solution of an acetate salt, but the $H^+$ acceptor is not limited thereto. Additionally, the $OH^-$ donor includes all of the materials capable of donating hydroxide ions to other materials, and specifically, the $OH^-$ donor may be a basic material (e.g., ammonia water, sodium hydroxide, lithium hydroxide, potassium hydroxide, etc.), but the $OH^-$ donor is not limited thereto.

Specifically, in the case of a pH control agent which is used in the process of preparing L-methionine crystals by increasing the pH (i.e., a step of pH readjustment) after the preparation of an acidic solution of L-methionine with a low pH (i.e., a step of pH adjustment), as the pH-lowering agent to be used in the pH adjustment, a $H^+$ donor such as a strong acid material (e.g., sulfuric acid, hydrochloric acid, etc.) may be used. Then, as the pH-increasing agent to be used in the step of pH readjustment for preparing L-methionine crystals, an $OH^-$ donor such as a basic material (e.g., ammonia water, sodium hydroxide, lithium hydroxide, potassium hydroxide, etc.) may be used. Additionally, since the hydrogen ion concentration in the solution is very high, an aqueous solution of a salt containing a $H^+$ acceptor, such as a conjugate base of a weak acid (e.g., an aqueous solution of an acetate salt), may be used, and as the conjugate base of the weak acid reduces the hydrogen ion concentration in the solution, the pH of the solution is increased, thereby improving the recovery rate.

Additionally, in the case of a pH control agent which is used in the process of preparing L-methionine crystals by lowering the pH (i.e., a step of pH readjustment) after the preparation of a basic solution of L-methionine with a high pH (i.e., a step of pH adjustment), as the pH-increasing agent to be used in the pH adjustment, an $OH^-$ donor such as a strong basic material (e.g., ammonia water, sodium hydroxide, lithium hydroxide, potassium hydroxide, etc.) may be used. Then, as the pH-lowering agent to be used in the step of pH readjustment for preparing L-methionine crystals, a $H^+$ donor such as an acidic material (e.g., sulfuric acid, hydrochloric acid, etc.) may be used. Additionally, since the hydroxide ion concentration in the solution is very high, an aqueous solution of a salt containing an $OH^-$ donor, such as a conjugate acid of a weak base (e.g., an aqueous solution of an ammonium salt), may be used, and as the conjugate acid of a weak base reduces the hydroxide ion concentration in the solution, the pH of the solution is lowered, thereby improving the recovery rate.

However, the pH control agent is not limited to the examples described above, but any pH control agent may be appropriately selected and used by those skilled in the art as long as L-methionine crystals can ultimately be obtained using the pH control agent without affecting the structure of L-methionine.

In the present disclosure, a pH-lowering agent may be added to the aqueous solution containing L-methionine so that the pH of the solution can be adjusted to a pH 1.0 to pH 3.5, and specifically pH 2.0 to pH 3.0; or a pH-increasing agent may be added to the aqueous solution containing L-methionine so that the pH of the solution can be adjusted to pH 7.5 to pH 10.0, and specifically pH 8.0 to pH 9.0, but the adjustment of the pH of the aqueous solution containing L-methionine is not limited thereto.

In the present disclosure, the amount of the pH-lowering agent to be added into the aqueous solution containing L-methionine is not limited as long as it can lower the pH of the solution, and the amount may be specifically 2 to 10 parts by weight, and more specifically 4 to 8 parts by weight relative to 300 parts by weight of water.

In the present disclosure, the amount of the pH-increasing agent to be added into the aqueous solution containing L-methionine is not limited as long as it can increase the pH of the solution, and the amount may be specifically 1 to 8 parts by weight, and more specifically 2 to 6 parts by weight relative to 300 parts by weight of water.

Step (b) is a step of heating an aqueous solution containing L-methionine to increase the solubility of L-methionine, and in the present disclosure, Step (b) is named "a step of heat treatment".

The step of heat treatment may be a step in which the aqueous solution containing L-methionine is specifically heated to a temperature of 40° C. to 90° C., more specifically 50° C. to 70° C., and even more specifically 55° C. to 65° C., but the temperature is not limited thereto.

Step (a) and Step (b) may be performed simultaneously, sequentially, or in reverse, and the order of performing these steps is not particularly limited. That is, a method in which L-methionine is added to an aqueous solution whose pH is already adjusted followed by heating, and a method in which an aqueous solution whose pH is already adjusted is heated and then L-methionine is added thereto fall within the scope of the present disclosure, and the time point of adding L-methionine does not affect the results of the present disclosure.

Finally, Step (c) is a step to extract L-methionine crystals from the aqueous solution containing L-methionine, which underwent pH adjustment and heat treatment, and in the present disclosure, Step (c) is named "a step of extraction of crystals".

As used herein, the term "crystallization" refers to a phenomenon in which a liquid or a solid in a non-crystalline state forms a crystal, and is accompanied by two phenomena called nucleation and crystal growth. Accordingly, Step (c) refers to a step in which crystal nuclei of L-methionine are formed, crystal nuclei of L-methionine are formed and grown, or the crystal nuclei formed from a previous step are grown, and L-methionine crystals can be obtained by Step (c).

The step of extraction of crystals may be performed by a crystallization method known in the art, such as methods of concentration by evaporation, cooling, adiabatic evaporation, addition of compounds, etc., but the crystallization method is not limited thereto.

The method for preparing L-methionine crystals of the present disclosure may further include a step of (b-2), in which a pH control agent is added to the aqueous solution containing L-methionine to increase or lower the pH (a step of pH readjustment) between Step (b) and Step (c) or in Step (c).

The bulk density of L-methionine crystals can be further increased via pH readjustment by adding a pH control agent in a state where the pH is already adjusted through Step (a).

In the step of pH readjustment of the present disclosure, L-methionine crystals can be formed through an instant pH increase/decrease by adding a pH control agent to an aqueous solution containing L-methionine.

In particular, in a case where the pH control agent used in the step of pH adjustment is a pH-increasing agent, the pH control agent used in the step of pH readjustment may be a pH-lowering agent, whereas in a case where the pH control agent used in the step of pH adjustment is a pH-lowering agent, the pH control agent used in the step of pH readjustment may be a pH-increasing agent.

Specifically, in a state where the solubility of L-methionine is increased according to the increase or decrease of the pH by the treatment of a pH control agent in the step of pH adjustment, the solubility of L-methionine may conversely be decreased according to the decrease or increase of the pH by the treatment of a pH control agent in the step of pH readjustment. As a result, crystallization of L-methionine (neutralization crystallization of L-methionine) may occur, and through such a process, the bulk density of L-methionine crystals (i.e., the final product) may be increased.

In the step of pH readjustment of the present disclosure, a pH-increasing agent may be added to the aqueous solution, whose pH was decreased in the step of pH adjustment, so as to readjust its pH to pH 2.0 to pH 5.0, and specifically to pH 3.0 to pH 4.0; or alternatively, a pH-lowering agent may be added to the aqueous solution, whose pH was increased in the step of pH adjustment, so as to readjust its pH to pH 6.0 to pH 9.0, and specifically to pH 7.0 to pH 8.0, but the step of pH readjustment is not limited thereto.

Additionally, the method for preparing L-methionine crystals of the present disclosure may further include a step of (b-1), in which a coagulant is added to the aqueous solution containing L-methionine (a step of addition of a coagulant), before Step (b-2) (i.e., a step of pH readjustment).

As described above, since neutralization crystallization is possible via Step (b-2) (i.e., a step of pH readjustment), the bulk density of L-methionine crystals may be increased by adding a coagulant before the step of pH readjustment so as to improve the efficiency of neutralization crystallization.

The coagulant may be specifically an aromatic compound, and more specifically, acetylsalicylic acid, acetaminophen, benzoic acid, salicylic acid, gallic acid, L-tyrosine, L-phenylalanine, or a combination thereof, but the coagulant is not limited thereto.

The coagulant may be added in an amount of 0.1 to 50 parts by weight, specifically 0.5 to 10 parts by weight, and more specifically 1 to 5 parts by weight relative to 300 parts by weight of L-methionine, but the amount of the coagulant is not limited thereto.

Furthermore, the method for preparing L-methionine crystals of the present disclosure may further include a step of (b-3) cooling the aqueous solution containing L-methionine (i.e., a step of cooling) before or during Step (c) (i.e., a step of extraction of crystals).

The cooling step is a step to cool the heat-treated aqueous solution containing L-methionine, and the crystallization of L-methionine can be induced by the cooling step. The cooling step may be performed before the step of extraction of crystals; alternatively, it may be performed simultaneously with the step of extraction of crystals or as the step of extraction of crystals itself in the step of extraction of crystals.

Additionally, the cooling step of the present disclosure may be performed after the step of pH readjustment. L-Methionine crystals with a significantly improved bulk density can be obtained by cooling the suspension which contains L-methionine crystals produced in the step of pH readjustment.

The cooling step may be to cool the heat-treated aqueous solution containing L-methionine to a temperature of 5° C. to 39° C., and specifically 15° C. to 35° C., and at a rate of 20° C./h or less, and specifically 12° C./h or less, 9° C./h or less, 6° C./h or less, 3° C./h or less, or 1° C./h or less, but the cooling step is not limited thereto.

Another aspect of the present disclosure is to provide L-methionine crystals which are prepared by the above method for preparing L-methionine crystals.

The L-methionine crystals and preparation method thereof are as described above.

DETAILED DESCRIPTION OF THE INVENTION

Hereinafter, the present disclosure will be described in detail through exemplary embodiments. However, these exemplary embodiments are provided only as a guide to the understanding of the present disclosure and are not intended to limit the scope of the present disclosure.

(1) Examples 1 and 2 and Comparative Example 1: Preparation of L-Methionine Crystals According to pH Adjustment

Example 1

After adding 6 g of sulfuric acid as a pH control agent to 300 g of water as a solvent, 45 g of L-methionine was dissolved at 60° C. to prepare an aqueous solution of L-methionine (pH 2.50). The solution was cooled to 30° C. at a rate of 6° C./h using a temperature control program in a constant-temperature bath to obtain L-methionine crystals. The BD of the obtained crystals was 370 g/L. In this Example, the BD was measured using the ABD Powder Characteristics Measuring Instrument (Tsutsui Scientific Instruments Corporation).

Example 2

After adding 4 g of sodium hydroxide as a pH control agent to 300 g of water as a solvent, 40 g of L-methionine was dissolved at 60° C. to prepare an aqueous solution of L-methionine (pH 8.15). The solution was cooled to 30° C. at a rate of 6° C./h using a temperature control program in a constant-temperature bath to obtain L-methionine crystals. The BD of the obtained crystals was 350 g/L.

Comparative Example 1

27 g of L-methionine was dissolved in 300 g of water as a solvent at 60° C. without using a pH control agent, and thereby a neutral aqueous solution of L-methionine was prepared. The solution was cooled to 30° C. at a rate of 6° C./h using a temperature control program in a constant-temperature bath to obtain L-methionine crystals. The BD of the obtained crystals was 190 g/L.

As illustrated in SEM images of L-methionine crystals in FIG. 1, it was confirmed that the BD of the L-methionine crystals prepared in Examples 1 and 2 and Comparative Example 1 was significantly increased according to pH adjustment of the aqueous solution of L-methionine.

The results of Examples 1 and 2 and Comparative Example 1 are summarized in Table 1 below.

TABLE 1

| Step | Additives and Others | Ex. 1 | Ex. 2 | Comp. Ex. 1 |
|---|---|---|---|---|
| Step of pH Adjustment | L-Methionine (Based on 300 g of Solvent) | 45 g | 40 g | 27 g |

TABLE 1-continued

| Step | Additives and Others | Ex. 1 | Ex. 2 | Comp. Ex. 1 |
|---|---|---|---|---|
| | pH Control Agent | Sulfuric Acid (6 g) | Sodium Hydroxide (4 g) | — |
| | pH | 2.50 | 8.15 | — |
| Step of Heat Treatment | Temperature | 60° C. | 60° C. | 60° C. |
| Step of Cooling | Temperature | 30° C. | 30° C. | 30° C. |
| | Cooling Rate | 6° C./h | 6° C./h | 6° C./h |
| | BD (g/L) | 370 | 350 | 190 |

(2) Examples 3 to 9 and Comparative Example 2: Preparation of L-Methionine Crystals by Treating an Acidic Solution of L-Methionine with Various Coagulants and pH-Increasing Agents Example 3

After adding 6 g of sulfuric acid as a pH control agent to 300 g of water as a solvent, 45 g of L-methionine was dissolved at 60° C. to prepare an aqueous solution of L-methionine (pH 2.50). 2 g of acetylsalicylic acid as a coagulant was added to the solution, and then 15 mL of an aqueous solution of ammonium acetate (a 1:1 mass ratio between ammonium acetate and water) as a second pH control agent was injected thereinto to obtain L-methionine crystals. In particular, the pH of the suspension was increased to pH 3.69 and the BD of the obtained L-methionine crystals was 610 g/L.

Example 4

L-Methionine crystals were obtained in the same manner as in Example 3, except that acetaminophen (2 g) was added as a coagulant instead of acetylsalicylic acid. The BD of the obtained L-methionine crystals was 590 g/L.

Example 5

L-Methionine crystals were obtained in the same manner as in Example 3, except that benzoic acid (2 g) was added as a coagulant instead of acetylsalicylic acid. The BD of the obtained L-methionine crystals was 590 g/L.

Example 6

L-Methionine crystals were obtained in the same manner as in Example 3, except that salicylic acid (2 g) was added as a coagulant instead of acetylsalicylic acid. The BD of the obtained L-methionine crystals was 580 g/L.

Example 7

L-Methionine crystals were obtained in the same manner as in Example 3, except that gallic acid (2 g) was added as a coagulant instead of acetylsalicylic acid. The BD of the obtained L-methionine crystals was 570 g/L.

Example 8

L-Methionine crystals were obtained in the same manner as in Example 3, except that L-tyrosine (2 g) was added as a coagulant instead of acetylsalicylic acid. The BD of the obtained L-methionine crystals was 570 g/L.

Example 9

L-Methionine crystals were obtained in the same manner as in Example 3, except that L-phenylalanine (2 g) was added as a coagulant instead of acetylsalicylic acid. The BD of the obtained L-methionine crystals was 560 g/L.

Comparative Example 2

L-Methionine crystals were obtained in the same manner as in Example 3, except that no coagulant was used. In particular, the BD of the obtained L-methionine crystals was 520 g/L.

The SEM images of the L-methionine crystals prepared in Examples 3 to 9 and Comparative Example 2 are illustrated in FIG. 2.

It was confirmed that the BD of the L-methionine crystals was significantly increased when the pH of the aqueous solution of pH-adjusted L-methionine was readjusted according to the addition of a coagulant regardless of the kind of the coagulant.

The results of Examples 3 to 9 and Comparative Example 2 are summarized in Table 2 below.

TABLE 2

| Step | Additives and Others (Based on 300 g of Solvent) | Ex. 3 | Ex. 4 | Ex. 5 | Ex. 6 | Ex. 7 | Ex. 8 | Ex. 9 | Comp. Ex. 2 |
|---|---|---|---|---|---|---|---|---|---|
| Step of pH Adjustment | L-Methionine | 45 g | 45 g | 45 g | 45 g | 45 g | 45 g | 45 g | 45 g |
| | pH-Lowering Agent (Sulfuric Acid) | 6 g | 6 g | 6 g | 6 g | 6 g | 6 g | 6 g | 6 g |
| | pH | 2.50 | 2.50 | 2.50 | 2.50 | 2.50 | 2.50 | 2.50 | 2.50 |

TABLE 2-continued

| Step | Additives and Others (Based on 300 g of Solvent) | Ex. 3 | Ex. 4 | Ex. 5 | Ex. 6 | Ex. 7 | Ex. 8 | Ex. 9 | Comp. Ex. 2 |
|---|---|---|---|---|---|---|---|---|---|
| Step of Heat Treatment | Temperature | 60° C. | 60° C. | 60° C. | 60° C. | 60° C. | 60° C. | 60° C. | 60° C. |
| Step of Addition of Coagulant | Acetylsalicylic Acid (=ASA); Acetaminophen (=AA); Benzoic Acid (=BA); Salicylic Acid (=SA); Gallic Acid (=GA); L-Tyrosine (L-Tyr); L-Phenylalanine (L-Phe) | ASA (2 g) | AA (2 g) | BA (2 g) | SA (2 g) | GA (2 g) | L-Tyr (2 g) | L-Phe (2 g) | — |
| Step of pH Readjustment | pH-Increasing Agent (50% Aqueous Solution of Ammonium Acetate) | 15 mL | 15 mL | 15 mL | 15 mL | 15 mL | 15 mL | 15 mL | 15 mL |
| | pH | 3.69 | 3.69 | 3.69 | 3.69 | 3.69 | 3.69 | 3.69 | 3.69 |
| Step of Extraction of Crystals | | Maintenance of Stirring at 60° C. | | | | | | | |
| | BD (g/L) | 610 | 590 | 590 | 580 | 570 | 570 | 560 | 520 |

(3) Examples 10 to 14 and Comparative Examples 3 to 7: Preparation of L-Methionine Crystals by Treating an Acidic Solution of L-Methionine with Coagulants and Various pH-Increasing Agents

Example 10

L-Methionine crystals were obtained in the same manner as in Example 3, except that 15 mL of an aqueous solution of lithium acetate (a 1:1 mass ratio between lithium acetate and water) was injected as a pH-increasing agent instead of ammonium acetate. In particular, the pH of the suspension was increased to pH 3.66 and the BD of the obtained L-methionine crystals was 580 g/L.

Comparative Example 3

L-Methionine crystals were obtained in the same manner as in Example 10, except that no coagulant was used. In particular, the BD of the obtained L-methionine crystals was 500 g/L.

Example 11

L-Methionine crystals were obtained in the same manner as in Example 3, except that 15 mL of an aqueous solution of sodium acetate (a 1:1 mass ratio between sodium acetate and water) was injected as a pH-increasing agent instead of ammonium acetate. In particular, the pH of the suspension was increased to pH 3.36 and the BD of the obtained L-methionine crystals was 550 g/L.

Comparative Example 4

L-Methionine crystals were obtained in the same manner as in Example 11, except that no coagulant was used. In particular, the BD of the obtained L-methionine crystals was 500 g/L.

Example 12

L-Methionine crystals were obtained in the same manner as in Example 3, except that 15 mL of an aqueous solution of potassium acetate (a 1:1 mass ratio between potassium acetate and water) was injected as a pH-increasing agent instead of ammonium acetate. In particular, the pH of the suspension was increased to pH 3.26 and the BD of the obtained L-methionine crystals was 560 g/L.

Comparative Example 5

L-Methionine crystals were obtained in the same manner as in Example 12, except that no coagulant was used. In particular, the BD of the obtained L-methionine crystals was 490 g/L.

Example 13

L-Methionine crystals were obtained in the same manner as in Example 3, except that 4.2 g of sodium hydroxide was injected as a pH-increasing agent instead of an aqueous solution of ammonium acetate. In particular, the pH of the suspension was increased to pH 3.43 and the BD of the obtained L-methionine crystals was 530 g/L.

Comparative Example 6

L-Methionine crystals were obtained in the same manner as in Example 13, except that no coagulant was used. In particular, the BD of the obtained L-methionine crystals was 450 g/L.

Example 14

L-Methionine crystals were obtained in the same manner as in Example 3, except that 7 mL of ammonia water was injected as a pH-increasing agent instead of an aqueous solution of ammonium acetate. In particular, the pH of the suspension was increased to pH 3.65 and the BD of the obtained L-methionine crystals was 600 g/L.

Comparative Example 7

L-Methionine crystals were obtained in the same manner as in Example 14, except that no coagulant was used. In particular, the BD of the obtained L-methionine crystals was 510 g/L.

The SEM images of the L-methionine crystals prepared in Examples 11 to 14 and Comparative Examples 3 to 7 are illustrated in FIG. 3.

It was confirmed that the BD of the L-methionine crystals was significantly increased when the pH of the aqueous solution of pH-adjusted L-methionine was readjusted, regardless of the kind of the pH control agent.

Additionally, the results of Examples 11 to 14 and Comparative Examples 3 to 7 are summarized in Table 3 below.

In particular, the pH of the suspension was decreased to pH 7.84 and the BD of the obtained L-methionine crystals was 500 g/L.

Comparative Example 8

L-Methionine crystals were obtained in the same manner as in Example 15, except that no coagulant was used. In particular, the BD of the obtained L-methionine crystals was 450 g/L.

Example 16

L-Methionine crystals were obtained in the same manner as in Example 15, except that 2 mL of sulfuric acid was injected as a pH-lowering agent instead of a 6:1 aqueous solution of ammonium acetate. In particular, the pH of the suspension was decreased to pH 7.46 and the BD of the obtained L-methionine crystals was 480 g/L.

TABLE 3

| Step | Additives and Others (Based on 300 g of Solvent) | Ex. 10 | Comp. Ex. 3 | Ex. 11 | Comp. Ex. 4 | Ex. 12 | Comp. Ex. 5 | Ex. 13 | Comp. Ex. 6 | Ex. 14 | Comp. Ex. 7 |
|---|---|---|---|---|---|---|---|---|---|---|---|
| Step of pH Adjustment | L-Methionine | 45 g | 45 g | 45 g | 45 g | 45 g | 45 g | 45 g | 45 g | 45 g | 45 g |
|  | pH-Lowering Agent (Sulfuric Acid) | 6 g | 6 g | 6 g | 6 g | 6 g | 6 g | 6 g | 6 g | 6 g | 6 g |
|  | pH | 2.50 | 2.50 | 2.50 | 2.50 | 2.50 | 2.50 | 2.50 | 2.50 | 2.50 | 2.50 |
| Step of Heat Treatment | Temperature | 60° C. | 60° C. | 60° C. | 60° C. | 60° C. | 60° C. | 60° C. | 60° C. | 60° C. | 60° C. |
| Step of Addition of Coagulant | Acetylsalicylic Acid (= ASA) | ASA (2 g) | — | ASA (2 g) | — | ASA (2 g) | — | ASA (2 g) | — | ASA (2 g) | — |
| Step of pH Readjustment | pH-Increasing Agent | 50% Aqueous Solution of Lithium Acetate (50 mL) | | 50% Aqueous Solution of Sodium Acetate (50 mL) | | 50% Aqueous Solution of Potassium Acetate (50 mL) | | Sodium Hydroxide (4.2 g) | | Ammonia Water (7 mL) | |
|  | pH | 3.66 | 3.66 | 3.36 | 3.36 | 3.26 | 3.26 | 3.43 | 3.43 | 3.65 | 3.65 |
| Step of Extraction of Crystals | | Maintenance of Stirring at 60° C. | | | | | | | | | |
|  | BD (g/L) | 580 | 500 | 550 | 500 | 560 | 490 | 530 | 450 | 600 | 510 |

(4) Examples 15 and 16 and Comparative Examples 8 and 9: Preparation of L-Methionine Crystals by Treating a Basic Solution of L-Methionine with Coagulants and Various pH-Lowering Agents

Example 15

After adding 4 g of sodium hydroxide as a pH control agent to 300 g of water as a solvent, 40 g of L-methionine was dissolved at 60° C. to prepare an aqueous solution of L-methionine (pH 8.15). 2 g of acetylsalicylic acid as a coagulant was added to the solution, and then 15 mL of an aqueous solution of ammonium acetate (a 6:1 mass ratio between ammonium acetate and water) as a pH-lowering agent was injected thereinto to obtain L-methionine crystals.

Comparative Example 9

L-Methionine crystals were obtained in the same manner as in Example 16, except that no coagulant was used. In particular, the BD of the obtained L-methionine crystals was 460 g/L.

The SEM images of the L-methionine crystals prepared in Examples 15 and 16 and Comparative Examples 8 and 9 are illustrated in FIG. 4.

It was confirmed that the BD of the L-methionine crystals was significantly increased when the pH of the aqueous solution of pH-increased L-methionine was readjusted, regardless of the kind of the pH-lowering agent added.

Additionally, the results of Examples 15 and 16 and Comparative Examples 8 and 9 are summarized in Table 4 below.

TABLE 4

| Step | Additives and Others (Based on 300 g of Solvent) | Ex. 15 | Comp. Ex. 8 | Ex. 16 | Comp. Ex. 9 |
|---|---|---|---|---|---|
| Step of pH Adjustment | L-Methionine | 40 g | 40 g | 40 g | 40 g |
| | pH-Increasing Agent (Sodium Hydroxide) | 4 g | 4 g | 4 g | 4 g |
| | pH | 8.15 | 8.15 | 8.15 | 8.15 |
| Step of Heat Treatment | Temperature | 60° C. | 60° C. | 60° C. | 60° C. |
| Step of Addition of Coagulant | Acetylsalicylic Acid (=ASA) | ASA (2 g) | — | ASA (2 g) | — |
| Step of pH Readjustment | pH-Lowering Agent | 15 mL of Aqueous Solution (ammonium acetate:water = 6:1) | | 2 mL of Sulfuric Acid | |
| | pH | 7.84 | 7.84 | 7.46 | 7.46 |
| Step of Extraction of Crystals | | Maintenance of Stirring at 60° C. | | | |
| | BD (g/L) | 500 | 450 | 480 | 460 |

(5) Examples 17 to 21 and Comparative Examples 10 and 11: Effects of Difference in Cooling Rate on BD Values of L-Methionine Crystals Example 17

After adding 6 g of sulfuric acid as a pH control agent to 300 g of water as a solvent, 45 g of L-methionine was dissolved at 60° C. to prepare an aqueous solution of L-methionine (pH 2.50). 2 g of acetylsalicylic acid as a coagulant was added to the solution, and then 15 mL of an aqueous solution of ammonium acetate (a 1:1 mass ratio between ammonium acetate and water) as a pH-increasing agent was injected thereinto to obtain a suspension in which L-methionine crystals were produced. In particular, the suspension was cooled to 30° C. at a rate of 12° C./h to obtain the final L-methionine crystals. The BD of the obtained L-methionine crystals was 690 g/L.

Example 18

L-Methionine crystals were obtained in the same manner as in Example 17, except that the suspension was cooled to 30° C. at a rate of 9° C./h instead of 12° C./h. The BD of the obtained L-methionine crystals was 730 g/L.

Example 19

L-Methionine crystals were obtained in the same manner as in Example 17, except that the suspension was cooled to 30° C. at a rate of 6° C./h instead of 12° C./h. The BD of the obtained L-methionine crystals was 750 g/L.

Example 20

L-Methionine crystals were obtained in the same manner as in Example 17, except that the suspension was cooled to 30° C. at a rate of 3° C./h instead of 12° C./h. The BD of the obtained L-methionine crystals was 760 g/L.

Example 21

L-Methionine crystals were obtained in the same manner as in Example 17, except that the suspension was cooled to 30° C. at a rate of 1° C./h instead of 12° C./h. The BD of the obtained L-methionine crystals was 800 g/L.

Comparative Example 10

L-Methionine crystals were obtained in the same manner as in Example 19, except that no coagulant was used. In particular, the BD of the obtained L-methionine crystals was 630 g/L.

Comparative Example 11

After adding 6 g of sulfuric acid as a pH control agent to 300 g of water as a solvent, 15 mL of an aqueous solution of ammonium acetate (a 1:1 mass ratio between ammonium acetate and water) was added thereto. 2 g of acetylsalicylic acid as a coagulant was added to the mixture and 45 g of L-methionine was dissolved in the mixture at 60° C. The thus-prepared solution was cooled to 30° C. at a rate of 6° C./h to obtain the final L-methionine crystals. The BD of the obtained L-methionine crystals was 410 g/L.

From the above Examples, it was confirmed that the BD values of the obtained L-methionine crystals were increased as the cooling rate became reduced, and from the experiment of Comparative Example 11, it was confirmed that the BD values obtained by the general cooling process were significantly reduced.

The SEM images of the L-methionine crystals prepared in Examples 17 to 21 and Comparative Examples 10 and 11 are illustrated in FIG. 5.

It was confirmed that the BD of the L-methionine crystals was significantly increased when the aqueous solution of pH-readjusted L-methionine was cooled.

In particular, it was confirmed that the L-methionine crystals obtained by the cooling crystallization process of the present disclosure showed significantly higher BD values compared to the L-methionine crystals obtained by a common cooling crystallization process in which the step of pH adjustment and the step of pH readjustment are absent.

Additionally, the results of Examples 17 to 21 and Comparative Examples 10 and 11 are summarized in Table 5 below.

TABLE 5

| Step | Additives and Others (Based on 300 g of Solvent) | Ex. 17 | Ex. 18 | Ex. 19 | Ex. 20 | Ex. 21 | Comp. Ex. 10 | Comp. Ex. 11 |
|---|---|---|---|---|---|---|---|---|
| Step of pH Adjustment | L-Methionine | 45 g | 45 g | 45 g | 45 g | 45 g | 45 g | L-Methionine (45 g), sulfuric acid, pH-increasing agent, and coagulant (the same as those in the left) are injected simultaneously in the step of pH adjustment and heated to 60° C. |
| | pH-Lowering Agent (Sulfuric Acid) | 6 g | 6 g | 6 g | 6 g | 6 g | 6 g | |
| | pH | 2.50 | 2.50 | 2.50 | 2.50 | 2.50 | 2.50 | |
| Step of Heat Treatment | Temperature | 60° C. | 60° C. | 60° C. | 60° C. | 60° C. | 60° C. | |
| Step of Addition of Coagulant | Acetylsalicylic Acid (=ASA) | ASA (2 g) | ASA (2 g) | ASA (2 g) | ASA (2 g) | ASA (2 g) | — | |
| Step of pH Readjustment | pH-Increasing Agent | 50% Aqueous Solution of Ammonium Acetate (15 mL) | | | | | | |
| | pH | 3.69 | 3.69 | 3.69 | 3.69 | 3.69 | 3.69 | |
| Step of Cooling | Temperature | 30° C. | 30° C. | 30° C. | 30° C. | 30° C. | 30° C. | 30° C. |
| | Cooling Rate (° C./h) | 12 | 9 | 6 | 3 | 1 | 6 | 6 |
| | BD (g/L) | 690 | 730 | 750 | 760 | 800 | 630 | 410 |

(6) Example 22 and Comparative Examples 12 and 13: Preparation of L-Methionine Crystals by Treating Aqueous Solution of L-Methionine with pH Control Agent (NaOH) and pH-Lowering Agent (Ammonium Acetate)

Example 22

After adding 4 g of sodium hydroxide as a pH control agent to 300 g of water as a solvent, 40 g of L-methionine was dissolved at 60° C. to prepare an aqueous solution of L-methionine. 2 g of acetylsalicylic acid as a coagulant was added to the solution, and then 15 mL of an aqueous solution of ammonium acetate (a 6:1 mass ratio between ammonium acetate and water) as a pH-lowering agent was injected thereinto to obtain a suspension in which L-methionine crystal nuclei were produced. The suspension was cooled to 30° C. at a rate of 6° C./h to obtain the final L-methionine crystals. The BD of the obtained L-methionine crystals was 700 g/L.

Comparative Example 12

L-Methionine crystals were obtained in the same manner as in Example 22, except that no coagulant was used. In particular, the BD of the obtained L-methionine crystals was 660 g/L.

Comparative Example 13

After adding 4 g of sodium hydroxide as a pH control agent to 300 g of water as a solvent, 15 mL of an aqueous solution of ammonium acetate (a 6:1 mass ratio between ammonium acetate and water) as a pH-lowering agent was added thereto. 2 g of acetylsalicylic acid as a coagulant was added to the mixture and 40 g of L-methionine was dissolved in the mixture at 60° C. The thus-prepared solution was cooled to 30° C. at a rate of 6° C./h to obtain the final L-methionine crystals. The BD of the obtained L-methionine crystals was 400 g/L.

The SEM images of the L-methionine crystals prepared in Example 22 and Comparative Examples 12 and 13 are illustrated in FIG. 6.

It was confirmed that the BD of the L-methionine crystals was significantly increased when the aqueous solution of pH-readjusted L-methionine was cooled.

In particular, it was confirmed that the L-methionine crystals obtained by the cooling crystallization process of the present disclosure showed significantly higher BD values compared to the L-methionine crystals obtained by a common cooling crystallization process in which the step of pH adjustment and the step of pH readjustment are absent.

Additionally, the results of Example 22 and Comparative Examples 12 and 13 are summarized in Table 6 below.

TABLE 6

| Step | Additives and Others (Based on 300 g of Solvent) | Ex. 22 | Comp. Ex. 12 | Comp. Ex. 13 |
|---|---|---|---|---|
| Step of pH Adjustment | L-Methionine | 40 g | 40 g | L-Methionine (40 g), sodium hydroxide, pH-lowering agent, and coagulant (the same as those in the left) are injected simultaneously in the step of pH adjustment and heated to 60° C. |
| | pH-Increasing Agent (Sodium Hydroxide) | 4 g | 4 g | |
| | pH | 8.15 | 8.15 | |
| Step of Heat Treatment | Temperature | 60° C. | 60° C. | |
| Step of Addition of Coagulant | Acetylsalicylic Acid (=ASA) | ASA (2 g) | — | |
| Step of pH Readjustment | pH-Lowering Agent | 15 mL of Aqueous Solution (ammonium acetate:water = 6:1) | | |
| | pH | 7.84 | 7.84 | |
| Step of Cooling | Temperature | 60° C. | 60° C. | 60° C. |
| | Cooling Rate (° C./h) | 6 | 6 | 6 |
| | BD (g/L) | 700 | 660 | 400 |

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A method for preparing L-methionine crystals, comprising:
    (a) adding a pH control agent to an aqueous solution comprising L-methionine to lower or increase the pH, a step of pH adjustment;
    (b) heating the aqueous solution comprising L-methionine, a step of heat treatment;
    (b-2) adding a pH control agent to the aqueous solution comprising L-methionine to increase or lower the pH, a step of pH readjustment, between Step (b) and Step (c) or in Step (c); and
    (c) extracting L-methionine crystals from the aqueous solution comprising L-methionine, which underwent pH adjustment and heat treatment, a step of extraction of crystals.

2. The method according to claim 1, further comprising Step (b-1): adding a coagulant to the aqueous solution comprising L-methionine, a step of addition of a coagulant, before Step (b-2).

3. The method according to claim 1, further comprising Step (b-3): cooling the aqueous solution comprising L-methionine, a step of cooling, before or during Step (c).

4. The method according to claim 1, wherein when the pH control agent in the step of pH adjustment is a pH-increasing agent, the pH control agent in the step of pH readjustment is a pH-lowering agent, and when the pH control agent in the step of pH adjustment is a pH-lowering agent, the pH control agent in the step of pH readjustment is a pH-increasing agent.

5. The method according to claim 2, wherein the coagulant is an aromatic compound.

6. The method according to claim 5, wherein the aromatic compound is at least one compound selected from the group consisting of acetylsalicylic acid, acetaminophen, benzoic acid, salicylic acid, gallic acid, L-tyrosine, and L-phenylalanine.

7. The method according to claim 2, wherein the coagulant is added in an amount of 2 to 7 parts by weight relative to 100 parts by weight of L-methionine.

8. The method according to claim 1, wherein the step of heat treatment is to heat to a temperature of 40° C. to 90° C.

9. The method according to claim 3, wherein the step of cooling is to cool to a temperature of 15° C. to 35° C.

10. The method according to claim 3, wherein the step of cooling is performed at a rate of 20° C./h or less.

11. The method according to claim 2, wherein when the pH control agent in the step of pH adjustment is a pH-increasing agent, the pH control agent in the step of pH readjustment is a pH-lowering agent, and when the pH control agent in the step of pH adjustment is a pH-lowering agent, the pH control agent in the step of pH readjustment is a pH-increasing agent.

* * * * *